United States Patent [19]

Wittkampf et al.

[11] 4,305,396
[45] Dec. 15, 1981

[54] RATE ADAPTIVE PACEMAKER AND METHOD OF CARDIAC PACING

[75] Inventors: Frederik H. M. Wittkampf; Kornelis A. M. Mensink, both of Brummen; Hendrik L. Brouwer, Geenwarden, all of Netherlands

[73] Assignee: Vitatron Medical B.V., Netherlands

[21] Appl. No.: 30,457

[22] Filed: Apr. 16, 1979

[51] Int. Cl.³ ............................................. A61N 1/36
[52] U.S. Cl. ............................................. 128/419 PG
[58] Field of Search .................... 128/419 PG, 419 PT

[56] References Cited

U.S. PATENT DOCUMENTS

| | | | |
|---|---|---|---|
| 3,517,663 | 6/1970 | Bowers et al. | 128/419 PG |
| 3,593,718 | 7/1971 | Krasner | 128/419 PG |
| 3,835,865 | 9/1974 | Bowers | 128/419 PG |
| 4,088,139 | 5/1978 | Auerbach | 128/419 PT |
| 4,091,817 | 5/1978 | Thaler | 128/419 PG |
| 4,096,865 | 11/1977 | Auerbach et al. | 128/419 PT |
| 4,114,628 | 9/1978 | Rizk | 128/419 PG |

OTHER PUBLICATIONS

Preston et al., "American Heart Journal", vol. 74, No. 2, Aug. 1967, pp. 233-242.
Koyama et al., "American Heart Journal", vol. 91, No. 4, Apr. 1976, pp. 457-459.
Westerholm, "Scandanavian Journal of Thoracic and Cardiovascular Surgery", 1971.

*Primary Examiner*—William E. Kamm
*Attorney, Agent, or Firm*—Woodcock, Washburn, Kurtz, Mackiewicz & Norris

[57] ABSTRACT

An improved automatically rate adaptive pacemaker, wherein the rate of delivered stimulus pulses is controlled as a function of sensed hearbeat characteristics and/or patient threshold. The pacemaker analyzes different characteristics or parameters of the detected heartbeat signal, and the rate of delivered stimulus pulses is controlled as a function of predetermined correlation factors. The pacemaker includes means for automatic threshold tracking, and also for adjusting the rate of delivered stimulus pulses as a continuous function of the patient threshold.

6 Claims, 1 Drawing Figure

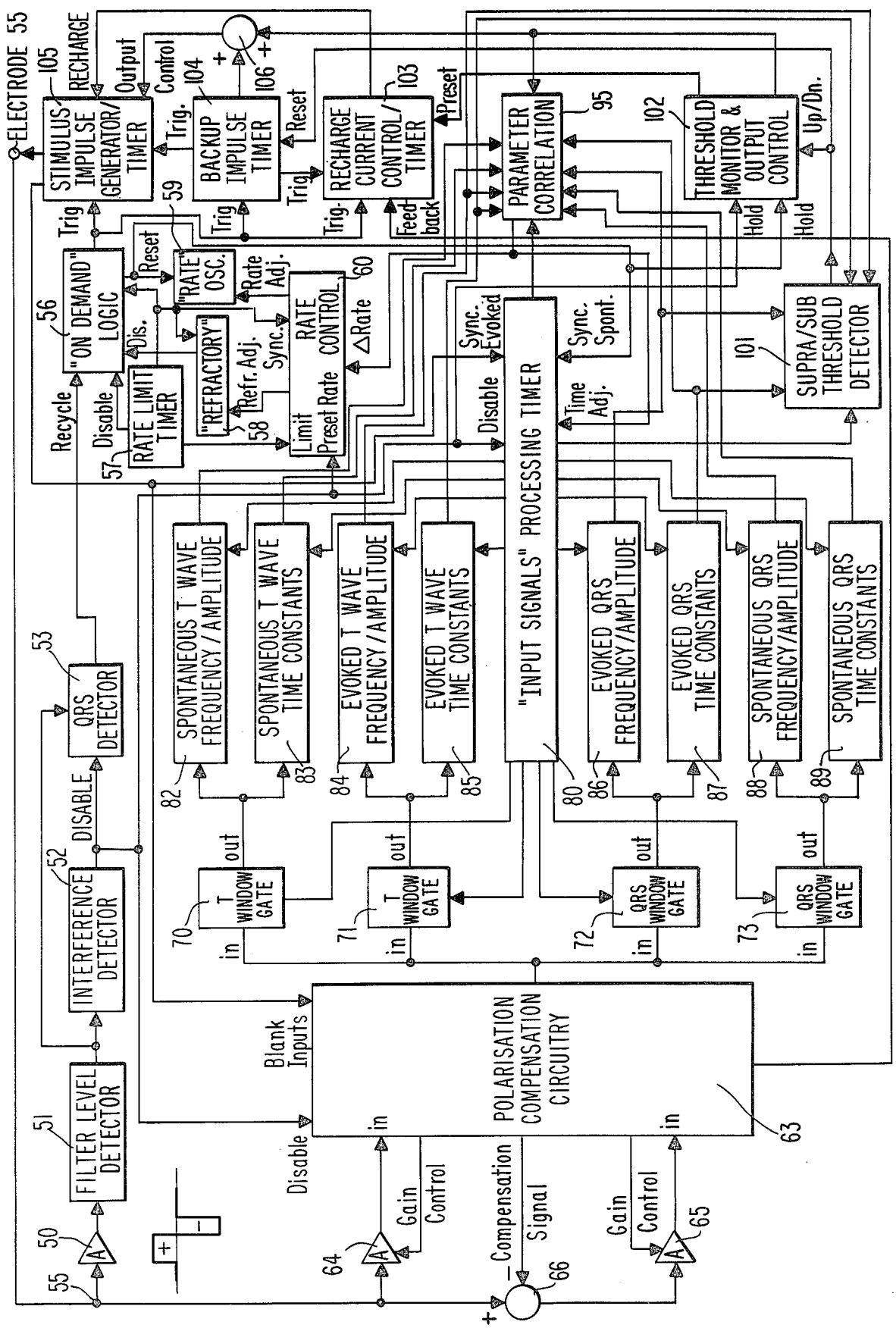

RATE ADAPTIVE PACEMAKER AND METHOD OF CARDIAC PACING

REFERENCE TO CO-PENDING APPLICATION

Reference is made to co-pending U.S. application Ser. No. 949,044, PHYSIOLOGICALLY ADAPTIVE CARDIAC PACEMAKER, filed Oct. 6, 1978, issued Oct. 21, 1980 as U.S. Pat. 4,228,803.

BACKGROUND OF THE INVENTION

This invention relates to pacemaker apparatus for delivering stimulus signals to a patient's heart, and in particular pacemaker apparatus adapted to vary the rate of the delivered stimulus signals as a function of sensed physiological changes.

As is set forth in the referenced U.S. Pat. No. 4,228,803, for a patient that is being stimulated by a cardiac pacemaker there is a correlation between optimum heart rate and the stimulus-T wave (S-T) time interval. Briefly, this time interval carries information relating to the patient's physiological condition, which information indicates the rate at which the patient's heart would beat if it were beating naturally and without a pacemaker. The sensing of a shortened S-T interval corresponds to a desired higher rate, and the sensing of a longer S-T interval corresponds to a desired lower rate. By continuously detecting the S-T interval and translating it into a correlating control signal, the rate of the pacer can be varied to provide delivered stimulus pulses at a desired rate more closely corresponding to that called for physiologically.

It has been determined that other information is contained in the heartbeat signal, and particularly the parameters of the QRS wave and the T wave, which can be used as input information for deriving rate control signals. For example, our analysis indicates that there is a rate correlation with both the frequency spectrum and the amplitude of the T wave. Generally, we believe that the larger the frequency composition, indicating a sharper T wave, the higher the desired heart rate. Likewise, the larger the observed peak amplitude of the T wave, the larger the desired heart rate. Another T wave parameter which is related to frequency spectrum is that of time interval, the interval of the T wave between defined leading and trailing reference levels. The smaller this time interval, corresponding to a larger frequency spectrum, the higher the desired heart rate, and vice versa. Likewise, the characteristics of the QRS wave are believed to correlate in generally the same manner. Thus, there are a number of parameters of the T wave and QRS wave which can be sensed and examined in order to obtain information for generation of a control signal which can in turn be used to modify or vary the rate of the stimulus generator used in the pacemaker. This observation leads to the conclusion of monitoring evoked QRS and T waves to continuously, i.e., from heartbeat to heartbeat, generate control signals for continuously controlling the pacemaker output rate. Additionally, the parameters of natural heartbeats may likewise be monitored while the pacemaker is in the inhibited mode, in the event it is desirable to place the pacemaker into a fixed rate mode upon the occurrence of predetermined circumstances.

Another correlating parameter which may be monitored is that of the patient's threshold to delivered stimulus pulses. As is well known in the pacing literature, threshold is defined as the level of the stimulus pulse required to evoke a resulting heartbeat when the pulse is delivered to the patient's heart. It has been determined that there is a correlation between the patient's threshold and certain physiological conditions, such as exercise, eating and sleeping. See "Changes in Myocardial Threshold. Physiologic and Pharmacologic Factors In Patients With Implanted Pacemakers", Preston et al, American Heart Journal, Vol. 74, No. 2, pp. 235–242, August, 1967; "Threshold Studies in Transvenous Cardiac Pacemaker Treatment", Westerholm, Scandanavian Journal of Thoracic and Cardiovascular Surgery, Supplementum 8, 1971. It is noted that the desired cardiac output of normal human subjects likewise varies as a function of exercise, eating and sleeping, leading us to the conclusion that there is a correlation between the patient's threshold and desired heart rate. It is widely accepted that the increase in cardiac output of normal patients is mainly supported by an increment in heart rate. "Initial Adjustment of Cardiac Output in Response to Onset of Exercise in Patients With Chronic Pacemaking as Studied by the Measurement of Pulmonary Blood Flow", Koyama et al, *American Heart Journal,* April, 1976, Vol. 91, No. 4, pp. 457–459.

From the above, it is seen that the foundation of the invention is that of capturing information available in a patient's heart signals detected at the pacing situs, and utilizing that information in order to control the paced heart rate corresponding to the patient's physiological condition. A pacemaker arrangement which provides for analysis of the various parameters of the QRS and T wave portions of the heart rate, as well as means for continuously tracking pacing threshold, provides the desired information. Means is thus provided for an automatically rate adaptive pacing system which utilizes to a maximum extent the available pertinent information derived from the heartbeat signal which is sensed by the same electrode which is used to deliver the pacing signal to the patient's heart.

SUMMARY OF THE INVENTION

It is a primary object of this invention to provide an improved pacemaker having means for sensing the patient's heartbeat signal and deriving therefrom a control signal for optimally controlling the rate of delivered stimulus pulses to the patient's heart.

It is another object of this invention to provide a pacemaker having means for tracking the patient's threshold to stimulus pulses, and means for controlling the rate of delivered stimulus pulses as a function of the tracked threshold.

It is a further object of this invention to provide a pacing system having means for monitoring the patient's threshold to delivered stimulus pulses to within very small variations, and having further means for controlling the rate of delivered stimulus pulses as a function of said monitored patient threshold. Additionally, the system includes an input having polarization compensation circuitry for facilitating detection of the presence or absence of evoked heartbeats, and means for delivering an output signal which includes at least a first recharge portion and a second stimulus portion.

In view of the above objects, there is provided a pacemaker system adapted to provide stimulus signals to and receive heartbeat signals from an electrode which is in operative contact with the patient's heart, the pacemaker having means for normally generating signals at a given rate and having rate control means responsive to said detected heartbeat signal, the rate control means being operative to adjust the operating rate of the delivered stimulus pulses as a predetermined function of selected parameters of the detected heartbeat signals. Specifically, the rate control means comprises a threshold tracking circuit which provides a signal which is representative of the patient threshold to delivered stimulus pulses, which representative signal is used in generation of the rate control signal.

BRIEF DESCRIPTION OF THE DRAWING

The FIGURE shows an overall block diagram of the pacemaker of this invention. The block diagram illustrates feedback paths for deriving information signals representing different parameters of detected heartbeat signals and also representing the patient threshold, and means for controlling the rate of generating and delivering stimulus pulses. The system is composed of a plurality of circuit blocks for carrying out respective functions with well known circuit techniques; the circuitry may be made with any suitable existing technology, i.e., discrete components, hybrid, or various types of monolithic arrangements. The essential aspects of the system as disclosed in the drawing are the control loops for carrying out a plurality of novel control functions. All of the control loops involve feedback from the electrode in the ventricle, or an equivalent electrode, to the stimulus generator, whereby the pacer rate is changed as a function of detected heartbeat signal characteristics following delivery of a stimulus pulse.

DESCRIPTION OF THE PREFERRED EMBODIMENT

Referring now to the drawing, there is illustrated a block diagram of an overall pacer system for carrying out the control features of this invention. The pacer system comprises the standard components of a "demand" pacer, as seen across the top level of the drawing. The detected heartbeat signal, which is sensed at electrode 55 within the heart, is amplified through amplifier 50 and connected to filter level detector 51. The output of detector 51 is connected to QRS detector 53, as well as to interference detector 52. Interference detectors are well known in the art, and may be configured with a plurality of different circuit designs. If interference is detected, the QRS detector is disabled so that the interference does not pass through to continuously recycle the pacemaker. The disable signal from detector 52 is also connected to other component blocks of the system, as discussed hereinbelow. The sensed QRS signal is connected to the "on demand" logic 56, to cause recycling of the rate oscillator 59 in a well known manner. As is conventional, the rate oscillator 59 normally times out after a predetermined interval if there is no intervening natural (spontaneous) QRS, at which time a timing signal is connected through the logic circuitry 56 to trigger stimulus impulse generator/timer 105, so as to cause delivery of an output signal. As is found in conventional pacemakers, a rate limit timer 57 is utilized to limit the pacer rate to a predetermined high limit. Also, a refractory interval circuit 58 is utilized to prevent the pacemaker from acting upon a sensed signal during the refractory interval. All of this portion of the pacemaker is conventional in demand pacers.

Stimulus impulse generator/timer block 105 comprises, in addition to conventional circuitry for determining the pulse width and the pulse level, means for generating an initial "recharge" portion of the delivered signal. As indicated, circuit 105 delivers to electrode 55 an output which suitably contains a first positive going portion for delivering a positive charge to compensate for the repolarization caused by the stimulus signal. The negative going portion of the signal from circuit 105 is the normal stimulus pulse, the negative going pulse being required to obtain a good capture. As is discussed in more detail below, the recharge portion of the pulse is used to facilitate sensing of the presence or absence of an evoked QRS signal shortly after the delivered stimulus pulse, so as to determine whether the stimulus pulse has actually evoked a response. Accurate sensing of whether or not there is an evoked response is essential to the threshold tracking feature of the system.

The remaining portion of the system illustrated in the drawing comprises, for the most part, components which are and constitute an addition to and an improvement over conventional pacemakers, demand or otherwise, for correlating the rate of delivered stimulus impulses to detected variations in the patient's heartbeat signal and to detected variations in patient threshold. Broadly speaking, the sensed signal is analyzed in blocks 82–89, each of which blocks is designed to analyze a respective different portion or parameter of the heartbeat signal. The outputs of these blocks constitute signals representing the sensed parameters, and are connected as inputs to parameter correlation block 95. At the same time, outputs of selected ones of the blocks 82–89 are connected to threshold detector circuit 101, which determines whether or not the last stimulus pulse has evoked a heartbeat. The output of block 101 is inputted to threshold monitor and output control circuit 102, which provides a threshold tracking signal representative of the state of the patient's threshold, which threshold signal is also inputted to parameter correlation block 95. The parameter correlation block weights the plural inputs in a predetermined manner and provides an output signal (Rate) to rate control circuit 60, which in turn provides a control signal to rate oscillator 59, thus closing the loop and controlling the pacer rate as a function of the selected sensed physiological conditions.

Examining the system in more detail, the input signal from electrode 55 is passed through amplifier 64 to the polarization compensation circuitry block 63. It is noted that the compensation circuitry is disabled when interference is detected, such that it produces no output in that circumstance. Blanking inputs are received from the stimulus generator 105, to signal the timing of the delivered stimulus pulse. These blanking inputs are utilized in the gain control lines connected to amplifiers 64 and 65, to prevent passage of the stimulus signal through to the compensation circuitry. The compensation circuitry is designed to subtract out the polarization component of the sensed signal, so that the QRS and T wave components can be more accurately detected. The compensation signal derived from circuitry 63 is connected to differential adder 66, to provide a compensated signal which is inputted to amplifier 65. Amplifier 65 is likewise gain controlled with the blanking inputs. Circuitry 63 in combination with amplifiers 64 and 65 thus produces an output heartbeat signal which is compensated to substantially subtract therefrom the polarization effect which is produced by the charge on the electrode following a delivered stimulus pulse. The polarization compensation circuitry is, in one aspect, not essential to the feedback system of this invention, in that other techniques known in the art may be used to obtain a good sharp heartbeat signal immediately following delivery of a stimulus pulse. However, it is necessary to provide means for deriving a good heartbeat signal from which the QRS and T waves can be accurately sensed, and for this purpose the compensation circuitry or its equivalent is required in order to have consistent and reliable system performance. Also, the recharge pulse preceeding the negative stimulus pulse, as illustrated in the lower left hand corner of the drawing, is an additional useful technique.

The detected heartbeat signal is connected from the output of circuitry 63 to window switches 70–73. Switches 70–73 are normally open switches, which close for respective time periods (windows) corresponding to the respective portions of the heartbeat signal which are to be analyzed by the succeeding circuits. The timing signals for controlling the operation of switches 70–73 are generated by the "input signals" processing timer 80. Note that timer 80 has as inputs a "sync evoked" signal and a "sync spont" signal. The sync evoked signal is taken from stimulus generator 105, and represents the leading edge of the stimulus pulse output. Thus, this signal provides means for the processing timer to generate a gating signal in any fixed relationship to the stimulus pulse. The sync spont signal is taken from the reset signal which resets the rate oscillator, and correspondingly represents detection of a spontaneous QRS. Thus, this signal enables the processing timer to generate a gating signal, or window in any timed relationship to the detected natural QRS signal. It is well known in the art that such gating signals, or windows, may be generated with multivibrators or the like.

The output of window gate 70 (the T wave portion of a spontaneous heartbeat signal) is connected to circuits 82 and 83. Circuit 82 is designed to detect the frequency composition and amplitude of a spontaneous T wave. The timing signal from timer 80 connected to circuit 82 is referenced to the spontaneous QRS signal, such that a window is provided at the expected time for the spontaneous T wave. Conventional circuitry is used for detecting the frequency composition, i.e., a filter which produces an output corresponding to the frequency spectrum under investigation. Alternately, the frequency may be judged by a slope or slew rate detector, to measure the steepness of either the leading or trailing edge. The amplitude may be detected by a conventional peak detector. In a similar manner, circuit 83 is gated to receive only the spontaneous T wave, and contains conventional circuitry for measuring predetermined time constants associated with the T wave. For example, the time period, or length of the T wave, such as between the time when it has risen to a predetermined voltage level and the time when it has fallen back to the same voltage level, may be determined, and a signal representing this time generated accordingly. Such a signal generator may be generated, as is well known, by a ramp generator which is initiated at the start of the time period and terminated at the end of the time period.

Circuits 84 and 85 receive inputs from gate 71, and receive further timing inputs from timer 80 which provide a reference to the time of delivery of the stimulus pulse. These circuits perform the same respective functions on the evoked T wave as circuits 82 and 83 perform on the spontaneous T wave. Circuits 86 and 87 receive inputs from gate 82, and also receive from timer 80 timing signals indicating the time of delivery of the stimulus pulse. The signals passed from gate 72 represent the QRS portion of the evoked response, and these circuits operate in the same manner as circuits 82, 83. Finally, circuits 88 and 89 receive the QRS portion of a spontaneous heartbeat signal as gated through gate 73, and provide outputs in the same manner as circuits 82 and 83, derived from such spontaneous QRS signal.

The outputs of circuits 82–89 are connected through as inputs to parameter correlation block 95. Also inputted to block 95, from block 102, is a signal representative of the patient threshold, as discussed below. The parameter correlation block comprises standard logic circuitry for providing an output signal which is a predetermined function of the 9 input signals it receives. By way of illustration, for each heartbeat signal variable the parameter correlation block suitably introduces a $\pm K$ factor, and then adds the 8 factored signals to get a $-$ Rate signal. Although a linear correlation for each input variable is assumed for illustrative purposes, it is understood that for some or all the variables of the correlation factor may be non-linear. Likewise, for a given pacemaker, the correlation factor for one or more of the input signals may be 0, i.e., such input variables are not utilized in determining the $-$ Rate signal.

In practice, it is known that during exercise the patient threshold drops. Since the heart rate normally rises during exercise, to provide an increased blood flow, there is a negative correlation, i.e., as the threshold goes down the indicated heart rate goes up, and as the threshold goes up, the indicated heart rate goes down. Further, it is well known that during sleeping and following eating the threshold goes up, and at this time the normal human heart rate goes down. Accordingly, the parameter correlation block 95 is designed to provide a $-K$ factor corresponding to the threshold level. For the heartbeat signal parameters, it is observed that for a signal with a larger frequency spectrum (i.e., taller and shorter) there is a higher desired body rate, and conversely a slower flatter signal (having a smaller frequency spectrum) corresponds to a lower desired body rate. Likewise, for the amplitude of the QRS or T wave portion of the heartbeat signal, a larger amplitude correlates with a higher desired heart rate and a smaller amplitude correlates with a lower desired heartbeat rate. It is known, of course, that there is a fixed relationship between frequency content of a signal and the time relationship, and thus shorter time constants associated with the QRS and T portions correspond to a larger frequency spectrum and a higher desired heartbeat rate, and vice versa. It follows that, for each of the 8 heartbeat parameter inputs to the parameter correlation block, the desired circuitry may simply multiply by a desired K factor, as by passing it through a standard amplifier, and fix the polarity of the resulting signal to $\pm$ by any well known circuit technique. The resulting signal is inputted to rate control circuit 60, which may be any conventional rate control circuit as is used in prior art programmable pacemakers. It is well known that such circuits can be utilized to control the rate of an oscillator as by adjusting the re-cycling voltage level of a standard oscillator, or, for example, by controlling the charging current of a timing oscillator. Rate control circuit 60 also may contain a memory to store the rate during periods when rate changes are inhibited.

The circuitry for providing threshold tracking is seen at the right hand portion of the drawing. Threshold detector 101 is designed to indicate whether the last delivered stimulus pulse was above or below threshold.

It is illustrated as receiving inputs from blocks 84, 85, 86 and 87, the four blocks which process evoked T wave or Q wave signals. In practice, the output from any one of the four evoked signal blocks may be used, it being desirable to use all four for purposes of redundancy and ensuring that in fact an evoked signal has been obtained. Detector 101 also receives from timer 80 a stimulus timing signal, indicating that a stimulus signal has been delivered. This is necessary so that the threshold detector can make a determination following each delivered stimulus. Reference is made to the patent literature which shows a number of threshold tracking circuits and systems, for details of various circuits utilized in such systems. In particular, reference is made to the U.S. Pat. to Bowers, No. 3,920,024, issued Nov. 18, 1975 to the assignee of this application.

The output of detector 101 is inputted to threshold monitoring and output control circuit 102. Circuit 102 contains an up/down counter, such as disclosed in the referenced patent to Bowers. The counter, being responsive to each up/down signal received provides a continuous record of the threshold. It is noted that, as in conventional threshold tracking systems, as long as a signal is evoked the impulse level is continuously dropped down until there is failure to evoke a heartbeat, following which the inpulse level is raised. The output of circuit 102 is connected both to the parameter correlation block 95, as discussed hereinbefore, and is connected through adder 106 to the output level control terminal of stimulus generator 105. Thus, the level of the stimulus delivered to the heart is continuously under the control of the threshold monitor control circuit 102. Note also that circuit 102 is held from movement whenever pacer operation is disabled due to detected interference, as well as whenever the pacemaker is in an inhibited mode due to sensed natural heartbeats.

The output from threshold detector 101 is also connected to the reset terminal of backup impulse timer 104. As long as the output of detector 101 indicates that a heartbeat has been evoked, the backup impulse timer is reset so that it does not deliver a backup impulse within a short time period following the regular stimulus pulse. However, if there is no evoked heartbeat, backup impulse timer is not reset, and delivers an output signal after a predetermined time period following the triggering of the stimulus impulse generator. The backup pulse may be, for example, delivered 50 or 100 ms following the stimulus pulse. As shown, a first output of backup circuit 104 is connected to circuit 106, to generate the output control signal to control the level of the next output delivered from stimulus generator 105. At the same time, a trigger signal is delivered from circuit 104 to trigger an output from circuit 105. If it is desirable to make the backup impulse twice the level of the last delivered stimulus pulse, circuit 106 may be a gate/amplifier circuit which multiplies by a factor of 2 the control signal coming from threshold circuit 102 whenever a backup pulse is delivered. Alternatively, the backup impulse circuit may simply open circuit 106, and deliver directly to the output control terminal of circuit 105 a signal requiring the maximum possible level for the backup stimulus. Reference is made to the aforementioned Bowers patent and to other patents dealing with threshold tracking systems for techniques used in controlling the timing and level of backup pulses. It is noted that the accuracy of the rate control loop of this invention depends upon the precision of measuring threshold, and for this reason circuit 102 is adapted to provide relatively small stimulus pulse variations, preferably in the area of millivolt varitions or equivalent current changes.

In an alternate embodiment, backup impulse circuit 104 is not resettable, and constantly delivers a backup pulse of twice the normal stimulus level following each delivered stimulus pulse.

Attention is directed to recharge current control/timer circuit 103. This circuit is used to generate the + recharge portion of the stimulus signal delivered to electrode 55 from circuit 105. The value of the recharge current pulse is controlled as a function of the negative going stimulus pulse, by connecting an output from threshold circuit 102 to the preset terminal of circuit 103. When the on demand logic 56 provides a trigger signal, calling for delivery of an output stimulus, this trigger signal is connected to circuit 103, which produces an output signal which is connected to stimulus impulse generator circuit 105. Suitably, the time relationship of the recharge portion and the stimulus portion of the output of circuit 105 is provided by introducing a delay in circuit 105, so that the negative going portion is initiated coincidentally with the end of the positive going portion. Alternately, the trailing edge of the positive recharge portion may be utilized to trigger the negative stimulus portion. Note that recharge circuit 103 is also triggered by the backup circuit 104, such that there is a recharge portion associated with each backup pulse as well. A feedback path is shown connecting an output from the compensation circuitry 63 to the recharge circuit 103, so that the value of the recharge current may be correlated with the amplitude of the sensed heartbeat signal. Thus, if the sensed heartbeat signal is very low, additional recharge current may be provided, and vice versa.

Another feature whereby the system is continuously adaptive to physiological changes is seen in the time adjust input signal to the timer 80. This signal, taken from the output of parameter correlation circuit 95, represents the rate control signal, and thus indicates to the timer when the stimulus rate is being increased or decreased, and how the S-T and QRS-T intervals are changing. This information may be used by the timer for adjusting the time relationship of each window to the synchronization signal, or for adjusting the duration of each window itself. Thus, as the pacing rate increases and decreases, the circuits 70–73 and 82–89 track the action, such as is done in a radar system, so that the windows for sensing different portions of the heartbeat signal remain properly aligned to such respective portions.

There is thus disclosed a pacing system, and method of pacing, wherein information is derived by analyzing a selected portion or portions of the detected heartbeat signal following delivery of a stimulus pulse, which information is utilized to generate a control signal for adjusting the pacer rate to adapt to physiological changes reflected by the heartbeat signal information. The system control loop preferably utilizes, as the source for detecting the heartbeat signal, the same electrode that is utilized for delivering the stimulus pulses. In referring to "the same electrode", in the preferred embodiment the lead which connects the pacemaker to the heart is either a unipolar or bipolar lead, having the electrode or electrodes positioned in the patient's ventricle. However, other lead designs may be utilized, and the system is not limited to the precise lead configuration. For example, the lead may incorporate a sensing electrode separate from the electrode used to deliver the stimulus pulses, for picking up the heartbeat signals. In the practice of the pacing system and method of this invention, there is no limitation upon the positioning of such sensing electrode except, of course, that it be positioned at a point within the patient's body where good sensing can be achieved.

It is to be understood that the parameter correlation function may be different for different pacer models, and more specifically may be adapted as a function of the patient in which the pacer is implanted. This invention embodies a system wherein the parameter correlation function is programmable from an external source, by known programming techniques. Thus, the pacemaker of this invention may be implanted in a patient, and at the time of implant or thereafter the exact parameter correlation functions may be determined and are set. This enables empirical observation of the performance of the pacer in the patient, so that the optimum parameter correlation functions can be established.

As used in the claims, the term "parameter" means a characteristic of a portion of the heart signal, and does not embrace the time interval between the Q and T wave portions (see referenced U.S. Pat. No. 4,228,803).

We claim:

1. A pacemaker having a stimulus generator for delivering pacing stimuli, means for controlling the stimulus rate of said delivered pacing stimuli, and threshold tracking means for tracking said patient's threshold to delivered stimuli, said pacemaker being characterized by having means for controlling said stimulus rate as a function of said tracked patient threshold.

2. The pacemaker described in claim 1, wherein said rate control means comprises means for providing a negative correlation between said patient threshold and said pacing rate, whereby as threshold goes up rate goes down and as threshold goes down rate goes up.

3. The pacemaker as described in claim 1, wherein said threshold tracking means comprises means for determining patient threshold to within an increment equal to or less than 100 millivolts.

4. The pacemaker as described in claim 1, wherein said rate control means comprises means for delaying the variation of rate in response to detected threshold.

5. The pacemaker as described in claim 1, wherein said stimulus generator comprises means for delivering a first positive recharge pulse and a second negative stimulating pulse, and means for controlling the amplitude of both said first and second pulses as a function of detected threshold.

6. A method of cardiac pacing of a patient wherein the rate of pacing is varied as a function of detected patient stimulus threshold, comprising:
   a. delivering pacing stimuli to a patient's heart, said stimuli being delivered at a controllable rate;
   b. tracking the threshold of said patient to delivered pacemaker stimuli; and
   c. controlling the rate of delivered stimuli as a function of said tracked patient threshold.

* * * * *

UNITED STATES PATENT AND TRADEMARK OFFICE
CERTIFICATE OF CORRECTION

PATENT NO. : 4,305,396
DATED : December 15, 1981
INVENTOR(S) : Frederik H. M. Wittkampf et al It is certified that error appears in the above-identified patent and that said Letters Patent are hereby corrected as shown below:

In the ABSTRACT, line 3, change "hearbeat" to -- heartbeat --.

Column 4, line 38, change "(Rate)" to -- ($\Delta$ Rate) --.

Column 6, line 18, change "- Rate" to -- $\Delta$ Rate --.

Column 6, line 24, change "- Rate" to -- $\Delta$ Rate --.

Signed and Sealed this

Twenty-seventh Day of April 1982

|SEAL|

Attest:

GERALD J. MOSSINGHOFF

Attesting Officer  Commissioner of Patents and Trademarks